(12) United States Patent
Harris

(10) Patent No.: US 10,398,817 B2
(45) Date of Patent: Sep. 3, 2019

(54) SUPPORT APPARATUS FOR BREAST PUMP

(71) Applicant: Crystal B. Harris, Charlotte, NC (US)

(72) Inventor: Crystal B. Harris, Charlotte, NC (US)

( * ) Notice: Subject to any disclaimer, the term of this patent is extended or adjusted under 35 U.S.C. 154(b) by 0 days.

(21) Appl. No.: 15/431,771

(22) Filed: Feb. 14, 2017

(65) Prior Publication Data

US 2017/0232165 A1    Aug. 17, 2017

Related U.S. Application Data

(60) Provisional application No. 62/295,170, filed on Feb. 15, 2016.

(51) Int. Cl.
*A41C 3/04* (2006.01)
*A61M 1/06* (2006.01)

(52) U.S. Cl.
CPC ............... *A61M 1/062* (2014.02); *A41C 3/04* (2013.01); *A61M 2209/088* (2013.01)

(58) Field of Classification Search
CPC ... A41C 3/04; A61M 1/062; A61M 2209/088; A41F 1/00; A41F 15/02; A41F 17/00; A41F 18/00; A41F 19/00; A41F 1/006; A61F 13/145
USPC ........................ 450/36, 32, 30, 37; 128/890; 604/74–79; 119/856, 857, 770, 792, 858; 2/267; 54/87; D2/624–626
See application file for complete search history.

(56) References Cited

U.S. PATENT DOCUMENTS

| | | | |
|---|---|---|---|
| 2,099,535 A * | 11/1937 | Rosow | A41F 1/00 2/96 |
| D126,899 S * | 4/1941 | Alberts | D2/624 |
| 5,575,768 A | 11/1996 | Lockridge | |
| 6,004,186 A | 12/1999 | Penny | |
| 6,135,853 A * | 10/2000 | Hopson | A41F 15/02 2/323 |
| 6,213,840 B1 | 4/2001 | Han | |
| 6,379,327 B2 | 4/2002 | Lundy | |
| 6,440,100 B1 | 8/2002 | Prentiss | |
| 7,950,980 B2 * | 5/2011 | Solberg | A61M 1/062 450/36 |
| 8,152,591 B2 * | 4/2012 | De Sousa | A41C 3/08 450/1 |
| 2007/0281585 A1 * | 12/2007 | Calamari | A41B 9/06 450/1 |
| 2008/0039781 A1 | 2/2008 | Bjorge | |

(Continued)

*Primary Examiner* — Alissa J Tompkins
*Assistant Examiner* — Brieanna T Szafran
(74) *Attorney, Agent, or Firm* — Sinha-Marsh Law Firm, P.C.; Rita K. Sinha-Marsh

(57) ABSTRACT

A support apparatus, which is fastened to the center and to the left and right straps of an article of clothing suitable for nursing (e.g. a nursing bra), and can be worn for extended periods of time (e.g. a full work day). The support apparatus is operable in an open and closed position. In its open position, it securely holds a breast pump's shield on a breast, enabling a woman to pump breast milk in a "hands-free" manner, while also allowing for translational motion of the breast shield. In its closed position, it lays flat against a woman's chest without obstructing access to her breasts, enabling the woman to breastfeed an infant while wearing it. By operating the two positions of the support apparatus, a woman has the option of pumping milk in a "hands-free" manner with one breast, and simultaneously breastfeeding an infant with the other breast.

14 Claims, 4 Drawing Sheets

(56) References Cited

U.S. PATENT DOCUMENTS

2016/0095967 A1* 4/2016 Weston ................ A61M 1/062
                                                    604/514
2016/0316826 A1* 11/2016 Sinh ...................... A41D 1/215

* cited by examiner

SUPPORT APPARATUS FOR BREAST PUMP

BACKGROUND OF THE INVENTION

Natural breastfeeding is widely accepted as the best way to nurture an infant. However, breastfeeding is not always possible for working mothers and other women who are not able to be present with infants at every feeding. In preparation for those moments, it is advantageous for breast milk to be expressed and stored for future consumption by the infant. Expression of breast milk with a pump has been a widely accepted practice for many years. Breast pumps range from simple hand operated models that pump one breast at a time to a wide selection of electric models now in use, most of which simultaneously pump both breasts. These pumps typically include: a funnel-shaped cup (called "a breast shield", which fits over the nipple and a substantial portion of the breast), a pump that generates an intermittent vacuum in the breast shield, and a container for the expressed breast milk. The intermittent suction generated by the pump within the breast shield causes a pulling or pressing of the breast, which is intended to mimic an infant's suckling action, thereby expressing milk.

Throughout history, articles of clothing have been adapted to simplify the task of nursing. Nursing attire (e.g. nursing bras, nursing shirts, nursing dresses, and nursing nightwear) contain flaps that can be unfolded to expose a portion of a breast. When using a breast pump, a woman must manually hold the breast shield on the exposed portion of the breast. Due to the length of time required to express milk when using the pump, women oftentimes pump both breasts simultaneously. The work intensive nature of pumping prevents women from performing other tasks for which their hands may be required. This problem could be greatly alleviated through the use of devices that pump breast milk in a "hands-free" manner, thereby freeing a woman's hands to perform other tasks while breast milk is being expressed. Clothing items have not yet fully remedied this task of "hands-free" breast pumping.

While there are a few "hands-free breast pumping bras" in existence, women are still challenged because these bras tend to be: uncomfortable to wear for long periods of time, unflattering to breasts underneath of clothes, and expensive in cost. These "hands-free breast pumping bras" also tend to limit a woman's ability to quickly switch back to breastfeeding if her infant demands, because the bra first needs to be removed completely before breastfeeding can begin. Finally, many of these bras and accompanying support devices prevent translational motion of the breast shield, thus preventing women from performing "hands-on pumping".

"Hands-on pumping" has become a proven technique (published as a ground-breaking study in the Journal of Perinatology by Jane Morton, et.al. in 2009) to express high levels of fat-rich, calorie-dense milk. This technique is accomplished when a woman stimulates breast tissue by massaging her breasts while pumping. Repositioning nipples and massaging breasts, while expressing milk, also has been proven to yield higher quantities of milk as the breast pump gains better access to different milk ducts. Yet, many factors make "hands-on pumping" a difficult feat. For example, while pumping, a woman can be prevented from positioning (and repositioning) her nipple at different angles if her hands are needed to hold the breast pump. Further, her "hands-free breast pumping bra" could cover too much of breast tissue, or thwart the translational motion of a breast shield.

Therefore, it is advantageous to develop a method and an apparatus that empowers a woman to wear any bra of her choice for any length of time, while having options on how to best nurse her infant. Whether she desires breastfeeding, "hands-free" breast pumping, or "hands-on pumping".

SUMMARY OF THE INVENTION

The principal objective of this invention is to provide a support apparatus that enables a woman to wear any article of clothing suitable for nursing, while having the options of: (1) breastfeeding an infant; (2) "hands-free" breast pumping; (3) "hands-on pumping" of her breast; or (4) all of the above, at the same time.

The Support Apparatus for Breast Pump can be fastened to a bra and worn underneath of clothing for extended periods of time (e.g. a full work day). It lays flat against a woman's chest without obstructing access to her breasts. Thereby enabling the woman to breastfeed an infant if she desires, while wearing the support apparatus. It further enables "hands-free" breast pumping by securely holding a breast pump's shield on a breast of a woman, without requiring the breast shield to be held by hands while pumping takes place. The breast shield is inserted through two extensions, which are designed to securely hold the breast shield on the breast. Because a woman's hands are not needed to hold the breast shield or breast pump in place, she is free to perform "hands-on pumping" if she desires, by using her hands to massage and compress her breasts. The support apparatus allows for translational motion of the breast shield, to further assist with expression of milk through her various milk ducts. Any of the described functions above can be performed on one breast or both breasts, individually or simultaneously.

This Support Apparatus is designed for use with: (1) any article of clothing suitable for nursing, such as "nursing attire" (i.e. attire containing flaps which can be unfolded to expose breasts) or any intimate attire that has straps and can easily expose breasts (e.g. sports bra, balconette bra, molded cup bra, shelf bra, etc); and (2) standard breast pump devices. The Support Apparatus fastens to the article of clothing without the use of an anchor disposed on the article of clothing. First, the Support Apparatus is fastened to the article of clothing at three points: around the right strap, around the left strap, and around the center panel. Then, it is operable in an OPEN or CLOSED position. In its OPEN position, its two extensions are pulled apart over one breast to securely hold a breast pump's shield on that breast. In its CLOSED position, it lays flat against a woman's chest without obstructing access to her breasts for breastfeeding.

A first embodiment of the invention: A support apparatus for a breast pump comprising:

a body configured to receive a breast pump, wherein the breast pump having a funnel section and a base section, the body including five separate extensions permanently connected at a center of the body: a front right extension, a back right extension, a front left extension, a back left extension, and a center extension;

a fastening system located on three of the five separate extensions: the front right extension, the front left extension, and the center extension, the fastening system operable to fasten the body to an article of clothing;

the fastening system comprising a first fastener coupled to the front right extension, the front left extension and the center extension, and a second fastener coupled to the front right extension, the front left extension and the center extension, wherein the first fastener on the front right extension releasably mates with the second fastener on the front right extension, the first fastener on the front left extension releasably mates with the second fastener on the front left extension, and the first fastener on the center extension releasably mates with the second fastener on the center extension, the front right extension and the back right extension being permanently connected at their outer edges, and the front left extension and the back left extension being permanently connected at their outer edges;

the front right extension being selectively moveable with respect to the back right extension permitting the passage of the breast pump's funnel section in between the front right extension and the back right extension, and the front left extension being selectively moveable with respect to the back left extension permitting the passage of the breast pump's funnel section in between the front left extension and the back left extension;

wherein the front right extension and the back right extension, and the front left extension and the back left extension, operatively position the breast pump's funnel section, configured to securely hold the breast pump's funnel section on a breast of a user while the fastening system simultaneously fastens the body to the article of clothing;

wherein the fastening system is operable to fasten the front right extension and the back right extension around a right strap of the article of clothing, the front left extension and the back left extension around a left strap of the article of clothing, and the center extension around a center panel of the article of clothing; and further wherein there are several said first fasteners and several said second fasteners on the front right extension and the front left extension, spaced apart equally.

A further embodiment of the invention as a method: A method of supporting a breast pump on a user, the method comprising:

(a) providing a breast pump having a base portion and a funnel portion;

(b) providing a support apparatus having a body configured to receive the breast pump having the funnel portion and the base portion, the body including five separate extensions permanently connected at a center of the body: a front right extension, a back right extension, a front left extension, a back left extension, and a center extension;

a fastening system located on three of the five separate extensions: the front right extension, the front left extension, and the center extension;

the fastening system comprising a first fastener coupled to the front right extension, the front left extension and the center extension, and a second fastener coupled to the front right extension, the front left extension and the center extension, wherein the first fastener on the front right extension releasably mates with the second fastener on the front right extension, the first fastener on the front left extension releasably mates with the second fastener on the front left extension, and the first fastener on the center extension releasably mates with the second fastener on the center extension, the front right extension and the back right extension being permanently connected at their outer edges, and the front left extension and the back left extension being permanently connected at their outer edges;

the front right extension being selectively moveable with respect to the back right extension permitting the passage of the breast pump's funnel section in between the front right extension and the back right extension, and the front left extension being selectively moveable with respect to the back left extension permitting the passage of the breast pump's funnel section in between the front left extension and the back left extension;

(c) fastening the five separate extensions to an article of clothing by using the fastening system;

wherein the fastening system is operable to fasten the front right extension and the back right extension around a right strap of the article of clothing, the front left extension and the back left extension around a left strap of the article of clothing, and the center extension around a center panel of the article of clothing; wherein there are several said first fasteners and several said second fasteners on the front right extension and the front left extension, spaced apart equally;

(d) pulling apart the front right extension from the back right extension or pulling apart the front left extension from the back left extension, and inserting the funnel portion of the breast pump between the front right extension and the back right extension or the front left extension and the back left extension, respectively; and (e) securing the funnel portion on a breast of the user.

These and other features and advantages of the present invention will be further understood upon consideration of the following detailed description of embodiments of the invention taken in conjunction with the drawings, in which:

Figure 1:
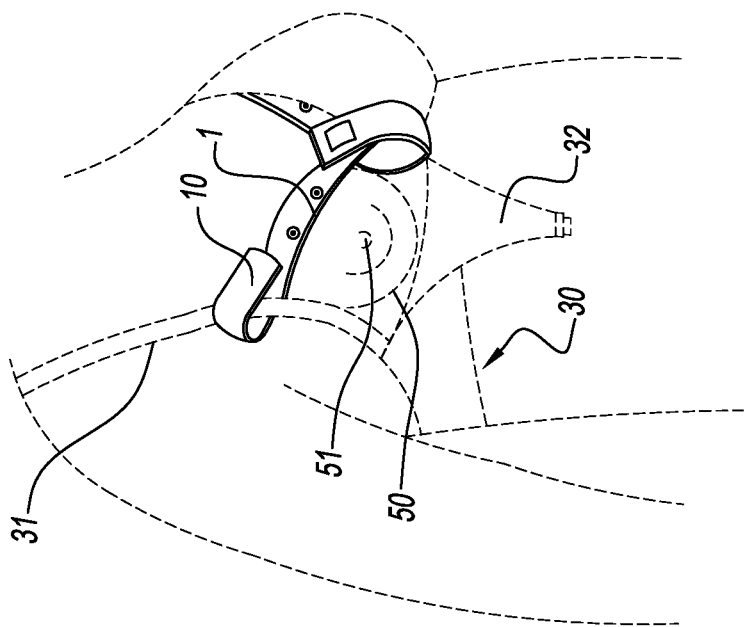
FIG. 1 is a side perspective view of the support apparatus fastened to a nursing bra. The support apparatus is in an OPEN position on one side, shown as securely holding a breast shield on a woman's right breast.

DETAILED DESCRIPTION OF THE DRAWINGS:

FIG. 1 is a side perspective view of the support apparatus fastened to a nursing bra. The support apparatus is in an OPEN position on one side, shown as securely holding a breast shield on a woman's right breast. Nursing bra 30 contains two flaps. Flap 32 is shown unfolded on one side to expose a right breast. A front extension 1 is pulled apart from a back extension 10 in a downward motion, creating an OPEN position of the support apparatus. A breast shield 41 of breast pump 40 is inserted through the two extensions, and placed on the breast. Front extension 1 and back extension 10 securely hold the breast shield 41 in place on this breast. This secure positioning enables a woman to pump breast milk in a "hands-free" manner.

While the breast pump 40 is securely held in place, the support apparatus does not impede on the translational motion of the breast shield 41, or on a woman's ability to massage and compress her breasts while pumping. A woman can freely reposition her breast, nipple, and breast shield at different angles while wearing the support apparatus. This freedom of motion yields higher quantities of expressed milk as the breast shield and breast pump can access different milk ducts, and the massaging of breasts can lead to the expression of high levels of fat-rich, calorie-dense milk. Most breast shields are roughly the same size in circumference, as is well known by those skilled in the art, however the elasticity of the support apparatus enables it to securely support breast shields of varying sizes.

While this embodiment shows the right breast being pumped, a woman can opt to instead pump the left breast by unfolding the left flap of nursing bra, and following the above steps to secure the breast shield 41 of breast pump 40 to the left breast. Additionally, the positioning of the front extension 1 and the back extension 10 can be switched, such that the back extension 10 can be pulled apart from the front extension 1 in the downward position. This alternate position also will securely hold the breast shield in place, and will not depart from the spirit of the invention.

Figure 2:
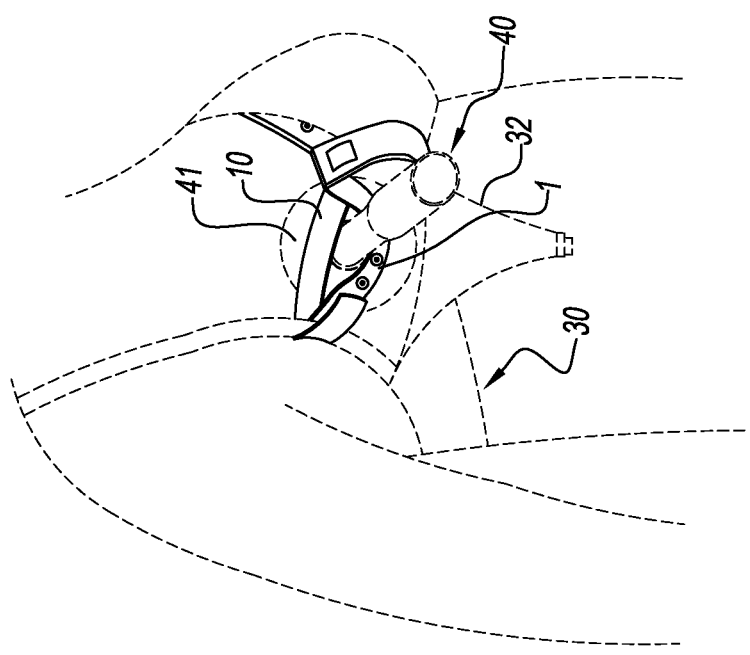
FIG. 2 is a side perspective view of the support apparatus fastened to a nursing bra. In contrast to FIG. 1, the support apparatus is shown in a CLOSED position, and a woman's right breast is fully exposed.

FIG. 2 is a side perspective view of the support apparatus fastened to a nursing bra. In contrast to FIG. 1, the support apparatus is now shown in a CLOSED position, with a woman's right breast fully exposed. Flap 32 is unfolded to expose breast 50 and nipple 51. Unlike the OPEN position of FIG. 1, the front extension 1 and the back extension 10 are not pulled apart, but rather laying flat against each other, creating the CLOSED position of support apparatus. In this position, the support apparatus lays flat against a woman's chest without obstructing access to her breasts, enabling the woman to breastfeed an infant while wearing it.

The two extensions can remain in this CLOSED position for extended periods of time (e.g. a full work day). This frees a woman from needing to change into and/or remove the support apparatus through the day, and frees a woman from needing to change into and/or remove her bra during the day. This freedom not only saves a woman ample time, but it grants to her flexibility, because she is afforded the option to wear any bra of her choice, for any duration of time.

As also previously shown in FIG. 1, the support apparatus is fastened to the nursing bra at three points: around the right strap, around the left strap, and around the center panel. Extensions 1 and 10 are fastened around the right strap 31 of nursing bra 30, above the right breast. (While not shown, the support apparatus is also fastened around the left strap of the nursing bra, above the left breast, in an identical manner). A center extension is shown fastened around the center panel of the nursing bra, displaying a label 4.

While the current embodiment shows the support apparatus fastened to a nursing bra, any attire containing flaps that can be unfolded to expose a breast, or any intimate attire that has straps and can easily expose breasts, is compatible for wear with the support apparatus.

Figure 3:
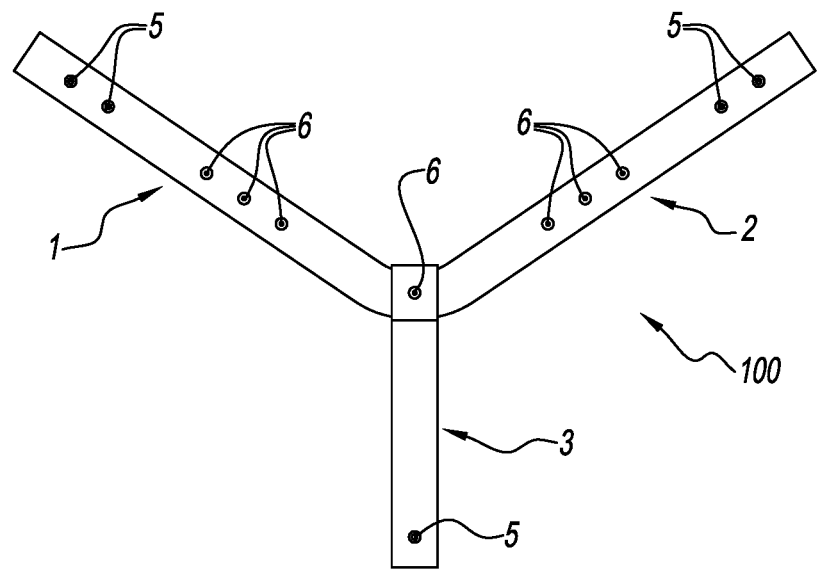
FIG. 3 is a front perspective view of the support apparatus constructed in accordance with this invention.

FIG. 3 is a front perspective view of the support apparatus 100 constructed in accordance with the invention. Shown are: a front extension 1, a front extension 2, and a center extension 3. These three extensions contain a fastening system on each of the extension ends. Shown are snap fasteners, but any fastening system that is well known to those skilled in the art can be used (e.g. hook-and-loop fasteners, hook and eye closures, buttons, clips, bra sliders, etc.). On the front extension 1 and front extension 2 are male halves 5 of snap fasteners, and female halves 6 of snap fasteners. Male halves 5 are spaced in accordance with female halves 6. While the current embodiment shows two male halves 5 and three female halves 6, the number of snap fasteners and the spacing of snap fasteners can vary according to preferences. On the center extension 3, a standard spacing exists between the male half 5 and female half 6.

Figure 4:
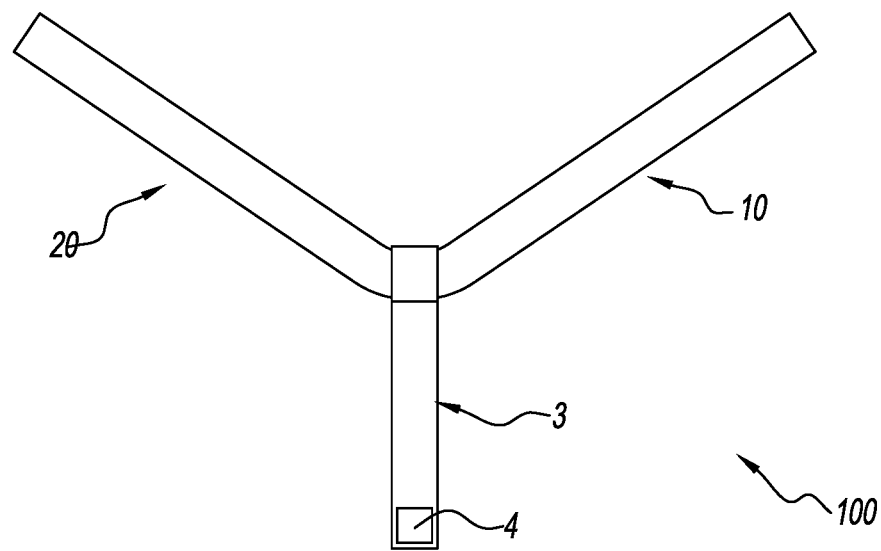
FIG. 4 is a back perspective view of the support apparatus shown in FIG. 3.

FIG. 4 is a back perspective view of the support apparatus shown in FIG. 3. Behind front extension 1 is a separate back extension 10. Behind front extension 2 is a separate back extension 20. The center extension 3 does not have a separate back extension, however the back of center extension 3 displays a label 4. Label 4 can be marked with arbitrary identifying indicia (e.g. a brand, a logo, care information, price information, etc.). The label can be made in any preferred color of design, customizable, stitched, or pre-printed. It is shown on center extension 3, but can be placed anywhere on the support apparatus.

The current embodiment of the support apparatus is constructed of nylon elastic material to enable maximum elasticity; however, it can be constructed of any material having similar or more proficient elasticity and adjustability properties, as would be well known to those skilled in the art. Support apparatus can be made in any preferred color or design, customizable or pre-printed. Extensions 1, 10, 2, 20, and 3 can vary in range of elasticity, as well as, in thickness and in size.

Figure 5:
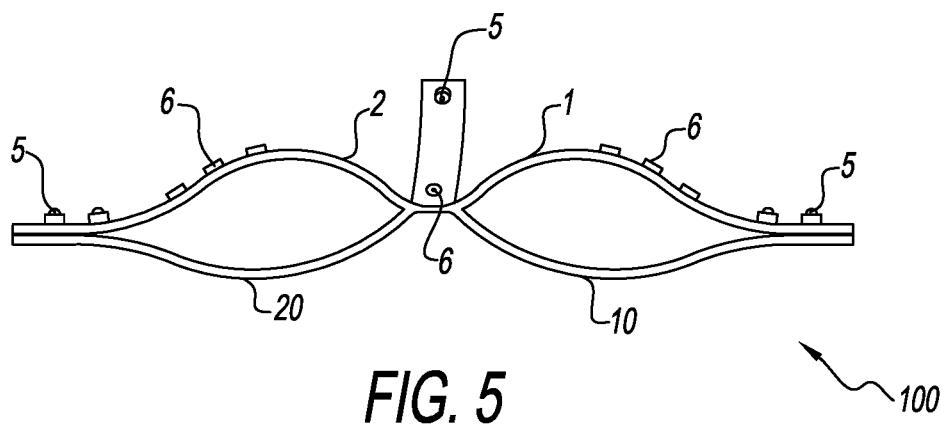
FIG. 5 is a top perspective view of the support apparatus shown in FIG. 3.

FIG. 5 is a top perspective view of the support apparatus shown in FIG. 3. Shown are three arms permanently connected at the center of the support apparatus 100: a right arm, a left arm, and a center arm. The front extension 1 and the back extension 10 also are permanently connected on their outer edges, creating the right arm of the support apparatus body. The front extension 2 and the back extension 20 also are permanently connected on their outer edges, creating a left arm of the support apparatus body. The third arm is a center arm, or described as the center extension 3.

Front extensions 1, 2 are operably moveable with respect to their corresponding back extensions 10, 20 as determined by the elasticity of the material used for the support apparatus. The distance between these front and back extensions can vary according to several additional variables such as: thickness, size, material, weight, etc. The permanent connection may be established through means of hand-stitching, machine-stitching, or any similar methods that are well known by those skilled in the art.

While the current embodiment describes the left and right arms being made of four pieces of material (extensions 1, 10, 2 and 20), in another embodiment, the left and right arms could be made from two pieces of material. Front extension 1 and front extension 2 could be made from one piece of material to constitute one front extension. Back extension 10 and back extension 20 could be made from a second piece of material to constitute one back extension. The front extension and the back extension would have a permanent connection at the center of support apparatus and a permanent connection at the two outer edges to create an identical shape as that shown in FIG. 5.

In yet another embodiment, the left and right arms could be made from one piece of material: either one long extension or one loop of material having no separations. When using one long extension, a permanent connection would be established at the center of support apparatus and at one outer edge to create an identical shape as that shown in FIG. 5. When a loop of material is used, the permanent connection would be established only at the center of the support apparatus, as a loop would already provide the additional permanent connections required to create an identical shape as that shown in FIG. 5.

The male halves 5 of snap fasteners and the female halves 6 of snap fasteners are shown on the three arms, and further described below in FIG. 6.

Figure 6:
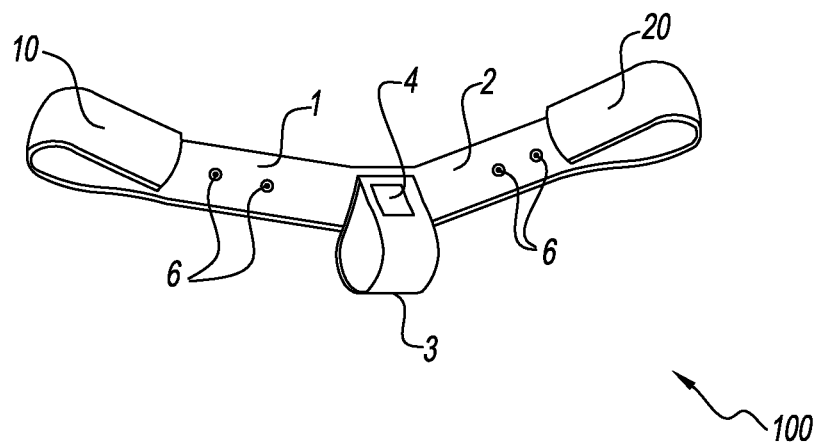
FIG. 6 is a front perspective view of the support apparatus shown in FIG. 3, depicted in a fastened state.

FIG. 6 is a perspective view showing the front of support apparatus 100 in a fastened state. The three arms are designed to fasten around a right strap, around a left strap and around the center panel of an article of clothing suitable for nursing (as shown fastened to a nursing bra in FIG. 1, FIG. 2, FIG. 7, and FIG. 8). When the right arm and the left arm are in fastened states, the front extensions 1 and 2 remain visible, and the back extensions 10 and 20 become visible. The male halves are releasably mated with the female halves of the snap fasteners, causing the back extensions to bend over and leaving the remaining female halves 6 visible. When the center arm 3 is in a fastened state, label 4 is displayed. Support apparatus must be fastened to an article of clothing suitable for nursing, prior to being used in either its OPEN or CLOSED positions.

The left arm and the right arm of support apparatus 100 can accommodate various breast sizes when adjusting the male and female snap fasteners. This adjustability is noteworthy because during nursing, breast sizes can increase and decrease, many times resulting in two different breast sizes. The left arm and the right arm can be adjusted independently to accommodate: (1) different sized breasts; (2) the unique pressure required for optimal "let down", or response to the breast pump; or (3) the varying weights of filled and unfilled breast pump containers. Less adjustability is required for the center arm, when fastened to the center panel of a bra because the size parameter is a standard size. Thus, only one male and female snap fastener is depicted on the center arm. However, additional snap fasteners can be used if size adjustability is required for the center arm.

Figure 7:
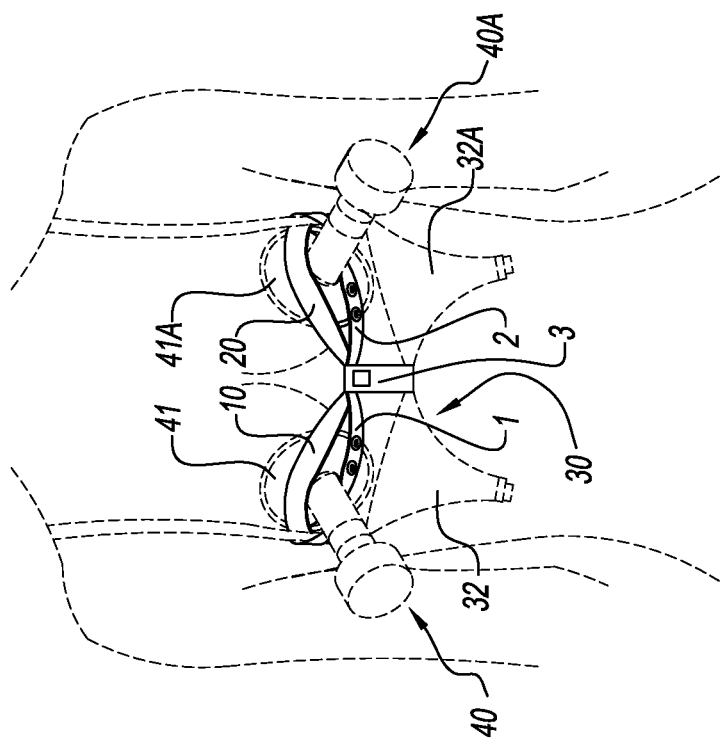
FIG. 7 is a front perspective view of support apparatus fastened to a nursing bra. It is shown in an OPEN position on both sides, securely holding two breast shields on a woman's left breast and right breast.

FIG. 7 shows a front view of another embodiment of the present invention, shown fastened to a nursing bra 30. Both breasts can be pumped simultaneously in a "hands-free" manner, by positioning both sides of support apparatus in the OPEN position and providing two breast pumps 40 and 40A. Both flaps 32 and 32A of nursing bra 30 can be unfolded to expose the left and right breasts. The front extension 1 is pulled apart from back extension 10 in a downward motion. The breast shield 41 is inserted between the two extensions, and placed on the breast, while the support apparatus securely holds the breast shield 41 and breast pump 40 in place on this breast. On the other side, the front extension 2 is pulled apart from back extension 20 in a downward motion. A second breast shield 41A is inserted between the two extensions, and placed on the other breast, while the support apparatus securely holds the breast shield 41A and breast pump 40A in place on this breast. Thus, both breasts could be pumped simultaneously in a "hands-free" manner, increasing the milk storage supply for future consumption.

Figure 8:
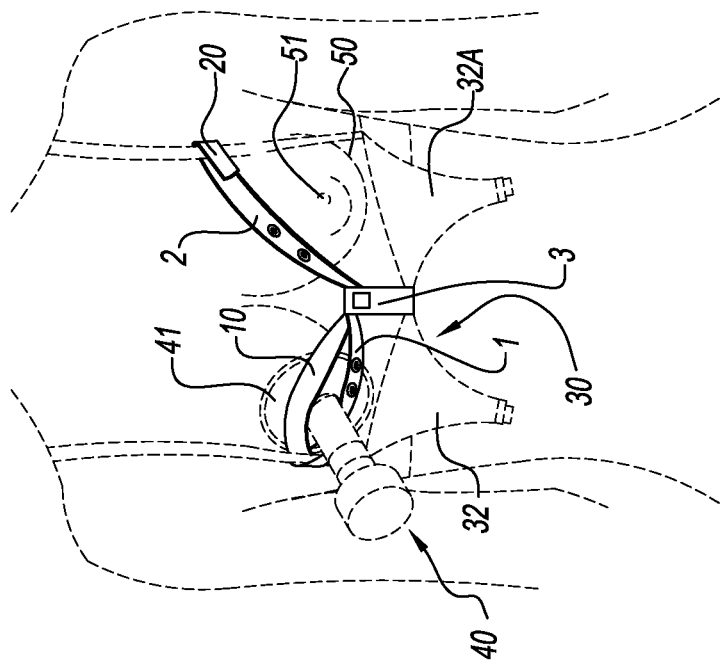
FIG. 8 is a front perspective view of support apparatus fastened to a nursing bra. It is in an OPEN position on one side, securely holding a breast shield on one breast; and in a CLOSED position on the other side, shown above the other breast, which is fully exposed.

FIG. 8 shows a front view of another embodiment of the present invention, while fastened to a nursing bra 30. A woman can pump one breast in a "hands-free" manner, and simultaneously breastfeed an infant with the other breast. On one side, a woman can unfold flap 32 of nursing bra 30 to expose her breast. The front extension 1 is pulled apart from back extension 10 in a downward motion. A breast shield 41 is inserted between the two extensions, and placed on the breast, while the support apparatus securely holds the breast shield 41 and breast pump 40 in place on this breast. This positioning enables a woman to pump breast milk in a "hands-free" manner on one breast. On the other side, flap 32A of nursing bra 30 is unfolded to expose breast 50 and nipple 51. In this position, the support apparatus lays flat against a woman's chest without obstructing access to her breasts, enabling the woman to breastfeed an infant while wearing it.

As stated above, the present invention enables a woman while wearing any attire of her choice suitable for nursing, to pump breast milk in a "hands-free" manner, by securely holding a breast pump to a breast while allowing for translational movement of the breast shield. The invention further allows for both breasts to be pumped simultaneously; or for one breast to be pumped, while the other is being used for breastfeeding, simultaneously. The closed position of the support apparatus enables it to be conveniently worn all day underneath of any attire.

It should be appreciated that the present invention may be modified or configured as appropriate for the application. The embodiments described above are to be considered in all respects only as illustrative and not restrictive. Changes may be made without departing from the spirit of the invention. The scope of the invention is indicated by the following claims rather than by the foregoing description. All changes which come within the literal meaning as well as the range of equivalency of the claims are to be embraced within their scope.

The invention claimed is:

1. A support apparatus for a breast pump comprising:
   a body configured to receive a breast pump, wherein the breast pump having a funnel section and a base section, the body including five separate extensions permanently connected at a center of the body: a front right extension, a back right extension, a front left extension, a back left extension, and a center extension;
   a fastening system located on three of the five separate extensions: the front right extension, the front left extension, and the center extension, the fastening system operable to fasten the body to an article of clothing;
   the fastening system comprising a first fastener coupled to the front right extension, the front left extension and the center extension, and a second fastener coupled to the front right extension, the front left extension and the center extension, wherein the first fastener on the front right extension releasably mates with the second fastener on the front right extension, the first fastener on the front left extension releasably mates with the second fastener on the front left extension, and the first fastener on the center extension releasably mates with the second fastener on the center extension,
   the front right extension and the back right extension being permanently connected at their outer edges, and the front left extension and the back left extension being permanently connected at their outer edges;
   the front right extension being selectively moveable with respect to the back right extension permitting the passage of the breast pump's funnel section in between the front right extension and the back right extension, and the front left extension being selectively moveable with respect to the back left extension permitting the passage of the breast pump's funnel section in between the front left extension and the back left extension;
   wherein, selectively, the front right extension and the back right extension or the front left extension and the back left extension operatively position the breast pump's funnel section to securely hold the breast pump's funnel section adaptively on a breast of a user while the fastening system simultaneously fastens the body to the article of clothing; and wherein the fastening system is operable to fasten the front right extension and the back right extension around a right strap of the article of clothing, the front left extension and the back left extension around a left strap of the article of clothing, and the center extension around a center panel of the article of clothing.

2. The support apparatus of claim 1, wherein the article of clothing is selected from the group consisting of: nursing bra, sports bra, balconette bra, molded cup bra, and shelf bra.

3. The support apparatus of claim 2, wherein the support apparatus fastens to the article of clothing without the use of an anchor disposed on the article of clothing.

4. The support apparatus of claim 3, wherein the front right extension, the back right extension, the front left extension, and the back left extension are configured to lay flat against a chest of the user.

5. The support apparatus of claim 3, wherein, selectively, the front right extension and the back right extension are pulled apart to insert the breast pump's funnel section in between the front right extension and the back right extension or the front left extension and the back left extension are pulled apart to insert the breast pump's funnel section in between the front left extension and the back left extension, adaptively onto the breasts of a user, while the fastening system simultaneously fastens the body to the article of clothing.

6. The support apparatus of claim 3, wherein the front right extension and the back right extension are configured to lay flat against the chest of a user, and the front left extension and the back left extension are pulled apart to insert the breast pump's funnel section in between the front left extension and the back left extension, adaptively onto the breast of a user, while the fastening system simultaneously fastens the body to the article of clothing.

7. The support apparatus of claim 1, wherein there are several said first fasteners and several said second fasteners on the front right extension and the front left extension, spaced apart equally.

8. The support apparatus of claim 1, wherein the fastening system is selected from the group consisting of: hook-and-loop fasteners, hook and eye closures, buttons, clips, and bra sliders.

9. A method of supporting a breast pump on a user, the method comprising:
(a) providing a breast pump having a base portion and a funnel portion;
(b) providing a support apparatus having a body configured to receive the breast pump having the funnel portion and the base portion, the body including five separate extensions permanently connected at a center of the body: a front right extension, a back right extension, a front left extension, a back left extension, and a center extension;
a fastening system located on three of the five separate extensions: the front right extension, the front left extension, and the center extension;
the fastening system comprising a first fastener coupled to the front right extension, the front left extension and the center extension, and a second fastener coupled to the front right extension, the front left extension and the center extension, wherein the first fastener on the front right extension releasably mates with the second fastener on the front right extension, the first fastener on the front left extension releasably mates with the second fastener on the front left extension, and the first fastener on the center extension releasably mates with the second fastener on the center extension,
the front right extension and the back right extension being permanently connected at their outer edges, and the front left extension and the back left extension being permanently connected at their outer edges;
the front right extension being selectively moveable with respect to the back right extension permitting the passage of the breast pump's funnel section in between the front right extension and the back right extension or the front left extension being selectively moveable with respect to the back left extension permitting the passage of the breast pump's funnel section in between the front left extension and the back left extension;
(c) fastening the five separate extensions to an article of clothing by using the fastening system;
wherein the fastening system is operable to fasten the front right extension and the back right extension around a right strap of the article of clothing, the front left extension and the back left extension around a left strap of the article of clothing, and the center extension around a center panel of the article of clothing;
(d) pulling apart the front right extension from the back right extension or pulling apart the front left extension from the back left extension, and inserting the funnel portion of the breast pump between the front right extension and the back right extension or the front left extension and the back left extension, respectively; and
(e) securing the funnel portion on a breast of the user.

10. The method of claim 9, wherein the article of clothing is selected from the group consisting of: nursing bra, sports bra, balconette bra, molded cup bra, and shelf bra.

11. The method of claim 10, wherein the support apparatus fastens to the article of clothing without the use of an anchor disposed on the article of clothing.

12. The method of claim 11, wherein the front right extension, the back right extension, the front left extension, and the back left extension are configured to lay flat against a chest of the user.

13. The method of claim 9, wherein there are several said first fasteners and several said second fasteners on the front right extension and the front left extension, spaced apart equally.

14. The method of claim 9, wherein the fastening system is selected from the group consisting of: hook-and-loop fasteners, hook and eye closures, buttons, clips, and bra sliders.

* * * * *